United States Patent [19]

Baird et al.

[11] 4,211,696

[45] Jul. 8, 1980

[54] DISPERSE MONOAZO DYESTUFFS DERIVED FROM 3,5-DINITRO-2-AMINO THIOPHENE AS DISAZO COMPONENT AND AN ARYLAMINE COUPLING COMPONENT

[75] Inventors: David B. Baird; Alan T. Costello; Brian R. Fishwick; Robert D. McClelland; Peter Smith, all of Manchester, England

[73] Assignee: Imperial Chemical Industries Limited, London, England

[21] Appl. No.: 656,593

[22] Filed: Feb. 9, 1976

Related U.S. Application Data

[63] Continuation-in-part of Ser. No. 488,242, Jul. 12, 1974, abandoned, which is a continuation-in-part of Ser. No. 324,189, Jan. 16, 1973, abandoned.

[30] Foreign Application Priority Data

Jan. 28, 1972 [GB] United Kingdom ................. 4046/72
Dec. 14, 1972 [GB] United Kingdom ............... 57675/72

[51] Int. Cl.$^2$ ..................... C09B 29/08; C09B 29/26; D06P 1/18; D06P 3/54
[52] U.S. Cl. .................................... 260/152; 549/68; 549/61; 549/69
[58] Field of Search ......................... 260/152

[56] References Cited

U.S. PATENT DOCUMENTS

| | | | |
|---|---|---|---|
| 2,683,708 | 7/1954 | Dickey et al. | 260/158 |
| 2,726,237 | 12/1955 | Towne et al. | 260/158 |
| 2,805,218 | 9/1957 | Towne et al. | 260/152 |
| 2,825,726 | 3/1958 | Towne et al. | 260/152 |
| 2,827,450 | 3/1958 | Towne et al. | 260/152 |

*Primary Examiner*—Floyd D. Higel
*Attorney, Agent, or Firm*—Cushman, Darby & Cushman

[57] ABSTRACT

Disperse monoazo dyestuffs, free from carboxylic and sulphonic acid groups, derived from 3,5-dinitro-2-amino thiophene as disazo component and an arylamine coupling component exhibit superior properties when used to give colorations to textile materials such as secondary cellulose acetate and cellulose triacetate, polyamide and aromatic polyester textile materials, said colorations having excellent fastness to light and to wet and dry heat treatments. The dyestuffs also have high tinctorial strength and excellent dyeing and build-up properties and produce depths of shade which are relatively independent of the dyebath pH, or the temperature of the dyebath or the liquor ratio of the dyebath.

3 Claims, No Drawings

DISPERSE MONOAZO DYESTUFFS DERIVED FROM 3,5-DINITRO-2-AMINO THIOPHENE AS DISAZO COMPONENT AND AN ARYLAMINE COUPLING COMPONENT

This Application is a Continuation-in-Part of our Application Ser. No. 488,242, which was filed in the U.S. Patent Office on July 12, 1974, now abandoned and which was itself a Continuation-in-Part of our Application Ser. No. 324,189 which was filed in the U.S. Patent Office on Jan. 16, 1973 and which is now abandoned.

This invention relates to disperse monoazo dyestuffs which are valuable for coloring synthetic textile materials.

According to the invention there are provided the disperse monoazo dyestuffs, free from sulphonic and carboxylic acid groups, which are of the formula:

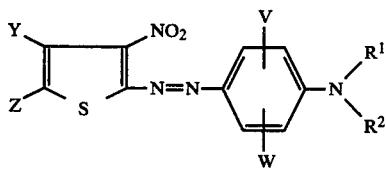

wherein
Y is selected from the group consisting of hydrogen, nitro, lower alkyl and nitrophenyl;
Z is selected from the group consisting of lower alkyl, phenyl, tolyl, nitrophenyl and nitromethylphenyl, nitro, cyano, lower alkoxycarbonyl, lower alkoxy lower alkoxy carbonyl, and

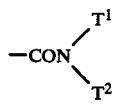

wherein
$T^1$ is selected from hydrogen, lower alkyl and phenyl and
$T^2$ is selected from hydrogen and lower alkyl;
V is selected from the group consisting of hydrogen, chlorine, lower alkyl, lower alkoxy and lower alkoxy carbonyl lower alkoxy;
W is selected from the group consisting of hydrogen, chlorine, bromine, lower alkyl, lower alkoxy lower alkyl, lower alkoxy carbonyl lower alkyl, lower alkoxy, lower alkoxycarbonyl lower alkoxy, lower alkylthio, lower alkoxycarbonyl lower alkylthio, lower alkoxy carbonyl, cyano, trifluoromethyl, lower alkylcarbonyl, lower alkylsulphonyl, benzoyloxy, lower alkylcarbonyloxy and N-lower alkyl carbonamido;
$R^1$ is selected from the group consisting of hydrogen, lower alkyl, cyano lower alkyl, lower alkoxy lower alkyl, lower alkoxy lower alkoxy lower alkyl, hydroxy lower alkyl, lower alkylcarbonyloxy lower alkyl, lower alkoxycarbonyl lower alkyl, lower alkoxy lower alkoxy carbonyl lower alkyl, benzoyloxy lower alkyl, lower alkoxy lower alkoxy lower alkoxy carbonyl lower alkyl, lower alkoxy carbonyl lower alkylamino carbonyloxy lower alkyl, lower alkylsulphonyloxy lower alkyl, phenyl lower alkyl and phenoxy lower alkyl; and $R^2$ is selected from the group consisting of hydrogen, lower alkyl, hydroxy lower alkyl, cyano lower alkyl, lower alkylcarbonyl lower alkyl, lower alkylcarbonyloxylower alkyl, hydroxy lower alkoxy lower alkyl, lower alkoxycarbonyl lower alkyl, lower alkoxy lower alkoxycarbonyl lower alkyl, lower alkoxy lower alkoxy lower alkoxycarbonyl lower alkyl, chloro lower alkyl, chloro hydroxypropyl, cyano lower alkoxy lower alkyl, lower alkoxycarbonyl lower alkoxy lower alkyl, lower alkoxy lower alkyl, lower alkoxy lower alkoxy lower alkyl, chloro lower alkylcarbonyloxy lower alkyl, hydroxy lower alkoxy lower alkyl, lower alkoxy lower alkyl carbonyloxy lower alkyl, phenyl lower alkyl, phenoxy lower alkyl, lower alkylsulphonyloxy lower alkyl, lower alkoxycarbonyloxy lower alkyl, lower alkoxycarbonyl lower alkylaminocarbonyloxy lower alkyl, lower alkylamino sulphonyl lower alkyl, di(lower alkoxycarbonyl)lower alkyl, phenyl, cyclopentyl, phenoxycarbonyl lower alkyl, lower alkylcarbonyloxy lower alkoxy lower alkyl, benzoyloxy lower alkyl and cyano lower alkoxy carbonyl lower alkyl.

Throughout this Specification the terms "lower alkyl" and "lower alkoxy" are used to denote alkyl and alkoxy radicals respectively containing from 1 to 4 carbon atoms.

As examples of the lower alkyl radicals represented by Y, Z, $T^1$, $T^2$, V, W, $R^1$ and $R^2$ there may be mentioned methyl, ethyl, n-propyl and n-butyl.

As examples of lower alkoxycarbonyl represented by Z and W there may be mentioned methoxycarbonyl, ethoxycarbonyl and butoxycarbonyl. As examples of lower alkoxy lower alkoxy carbonyl represented by Z there may be mentioned β-methoxyethoxycarbonyl and γ-ethoxypropoxycarbonyl.

As examples of lower alkoxy represented by V there may be mentioned propoxy, ethoxy and, above all, methoxy. As an example of lower alkoxycarbonyl lower alkoxy represented by V there may be mentioned β-methoxycarbonylethoxy. Preferably V is hydrogen, lower alkyl or lower alkoxy, and, above all, V is hydrogen, methyl or methoxy.

As specific examples of the various radicals represented by W there may be mentioned lower alkoxy lower alkyl such as β-ethoxyethyl and γ-methoxypropyl; lower alkoxycarbonyl lower alkyl such as β-(methoxycarbonyl)ethyl, lower alkoxy such as propoxy, ethoxy and, above all, methoxy; lower alkoxycarbonyl lower alkoxy such as β-(methoxycarbonyl)ethoxy; lower alkylthio such as methylthio and ethylthio; lower alkoxycarbonyl lower alkylthio such as β-(ethoxycarbonyl)ethylthio; lower alkylcarbonyl such as acetyl and propionyl; lower alkylsulphonyl such as methylsulphonyl, ethylsulphonyl and butylsulphonyl; lower alkylcarbonyloxy such as acetoxy; and N-lower alkylcarbonamido such as N-ethylcarbonamido.

Preferably W is hydrogen, chlorine, bromine, lower alkyl, lower alkoxy, lower alkoxycarbonyl, lower alkylcarbonyl, cyano or trifluoromethyl. Above all W is hydrogen, chlorine, bromine, lower alkyl (in particular methyl) or lower alkoxy (in particular methoxy).

Preferably V is attached to the benzene ring in ortho position to the

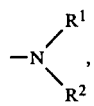

and W is in para position to V.

As specific examples of the

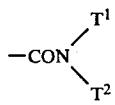

groups represented by Z there may be mentioned N-methylcarbonamido and N:N-diethylcarbonamido.

As specific examples of the various radicals represented by $R^1$ and/or $R^2$ there may be mentioned hydroxy lower alkyl such as β-hydroxyethyl, β- or γ-hydroxypropyl and ω-hydroxybutyl; cyano lower alkyl such as β-cyanoethyl; chloro lower alkyl such as β-chloroethyl and β- or γ- chloropropyl; lower alkoxy lower alkyl such as β-(methoxyor ethoxy-) ethyl, γ-methoxypropyl and ω-ethoxybutyl; lower alkylcarbonyl lower alkyl such as β-acetoxyethyl and ω-acetoxybutyl; phenyl lower alkyl such as benzyl and β-phenylethyl; lower alkoxy lower alkoxy lower alkyl such as β-(β'-methoxyethoxy)ethyl; hydroxy lower alkoxy lower alkyl such as β-(β'-hydroxyethoxy)ethyl; lower alkoxycarbonyl lower alkyl such as β-methoxycarbonylethyl, β-ethoxycarbonylethyl and γ-methoxycarbonylpropyl; lower alkoxy lower alkoxy carbonyl lower alkyl such as β-(β'-methoxyethoxycarbonyl)ethyl and γ-(β'-ethoxy carbonefethoxy)propyl; benzoyloxy lower alkyl such as β-(benzoyloxy)ethyl; phenoxy lower alkyl such as β-phenoxyethyl; lower alkoxy lower alkoxy lower alkoxycarbonyl lower alkyl such as β-[β'-(β''-ethoxyethoxy)ethoxycarbonyl]ethyl; lower alkylcarbonyl lower alkyl such as β-acetylethyl; cyano lower alkoxy lower alkyl such as β-(β'-cyanoethoxy)ethyl; lower alkoxycarbonyl lower alkoxy lower alkyl such as β-(β'-ethoxycarbonylethoxy)ethyl; chloro lower alkylcarbonyloxy lower alkyl such as β-(chloroacetoxy)ethyl; hydroxy lower alkoxy lower alkyl such as β-(β'-hydroxyethoxy)ethyl; lower alkoxy lower alkylcarbonyloxy lower alkyl such as β-(methoxypropionyloxy)ethyl; lower alkylsulphonyloxy lower alkyl such as β-(methylsulphonyloxy) ethyl; lower alkoxycarbonyloxy lower alkyl such as β-(methoxycarbonyloxy) ethyl; lower alkoxycarbonyl lower alkylaminocarbonyloxy lower alkyl such as β-[N-(β'-ethoxycarbonylethyl)aminocarbonyloxy]ethyl; lower alkylaminosulphonyl lower alkyl such as β-(methylaminosulphonyl)ethyl; di(lower alkoxycarbonyl) lower alkyl such as α-β-di(methoxycarbonyl) ethyl; phenoxycarbonyl lower alkyl such as β-(phenoxycarbonyl)ethyl; lower alkylcarbonyloxy lower alkoxy lower alkyl such as β-(β'-acetoxyethoxy)ethyl; and cyano lower alkoxy carbonyl lower alkyl such as β-(β'-cyanoethoxycarbonyl)ethyl. Preferably $R^1$ is selected from the group consisting of hydrogen, lower alkyl, cyano lower alkyl, lower alkyl carbonyloxy lower alkyl, lower alkoxycarbonyl lower alkyl, lower alkoxy lower alkoxycarbonyl lower alkyl, lower alkoxy lower alkyl and phenyl lower alkyl; whilst $R^2$ is preferably selected from the group consisting of lower alkyl, hydroxy lower alkyl, cyano lower alkyl, lower alkyl carbonyloxy lower alkyl, lower alkoxy carbonyl lower alkyl, lower alkoxy lower alkoxycarbonyl lower alkyl, lower alkoxy lower alkyl and phenyl lower alkyl.

It is however preferred that $R^1$ and $R^2$ together contain not more than one hydroxy group.

According to a further feature of the invention there is provided a process for the manufacture of the azo dyestuffs as hereinbefore defined which comprises diazotizing an amine of the formula:

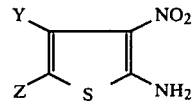

Formula I and coupling the resulting diazo compound with a coupling component of the formula

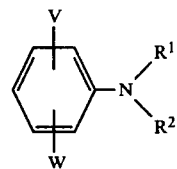

Formula II wherein Y, Z, V, W, $R^1$ and $R^2$ have the meanings stated, the amine and coupling component being free from carboxylic and sulphonic acid groups.

The process can be carried out by conventional methods. For example, the process of the invention can be conveniently carried out by adding sodium nitrite to a solution or dispersion of the amine in a strong inorganic acid or an aqueous solution thereof, or, by preferably stirring the amine with nitrosylsulphuric acid, and adding the resulting solution or dispersion of the diazo component to a solution of the coupling component in water or in a mixture of water and a water-miscible organic liquid, if necessary adjusting the pH of the mixture to facilitate the coupling reaction, and finally isolating the resulting dyestuff by conventional methods.

The amides of Formula I can themselves be obtained by the conventional methods used for the production of thiophene derivatives. Thus, for example, a 2-halogenothiophene can be nitrated, and the halogen atom in the 2-position then converted to an amino group by treatment with ammonia. Alternatively the 2-aminothiophenes containing electron withdrawing groups can be prepared by conventional methods from the thiophenes obtained by the methods described in Chemische Berichte, Volume 98 at page 3571 (1965) and Volume 99 at page 94 (1966).

As specific examples of amines of Formula I there may be mentioned, for example, 2-amino 3:5-dinitrothiophene, 2-amino-3:4:5-trinitrothiophene, 3-nitro-5-(carbonamido- or methoxycarbonyl)-2-aminothiophene, 3:5-dinitro-4-methyl-2-aminothiophene and 3:5-dinitro-4-(methoxy- or ethoxy-carbonyl)-2-aminothiophene. The preferred amine for use in the process is 2-amino-3:5-dinitrothiophene.

As examples of coupling components of Formula II there may be mentioned 2:5-dimethoxyaniline, N:N-diethylaniline, N:N-di(β-acetoxyethyl)-m-toluidine, N-ethyl-N-(β-hydroxyethyl)-m-aminoacetanilide, N:N-di(β-methoxycarbonylethyl)aniline, N-ethyl-N-(β-cyanoethyl)aniline, N:N-di(β-acetoxyethyl)-m-chloroaniline, N-ethyl-N-(β-butoxycarbonylethyl)aniline, N-[β-(β'-methoxyethoxycarbonyl)ethyl]-m-toluidine and N-[β-(β'-hydroxyethoxycarbonyl)ethyl]-m-aminoacetanilide.

A preferred class of the dyestuffs of the invention comprises the dyestuffs wherein Y is hydrogen and Z is nitro.

A second preferred class of the dyestuffs of the invention comprises the dyestuffs of the formula:

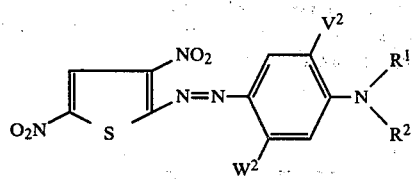

wherein $R^1$ and $R^2$ have the meanings stated above, $V^2$ is hydrogen, lower alkyl or lower alkoxy, and $W^2$ is hydrogen, chlorine, bromine, lower alkyl, lower alkoxy or trifluoromethyl.

The azo dyestuffs of the invention are valuable for coloring synthetic textile materials in particular secondary cellulose acetate and cellulose triacetate textile materials, polyamide textile materials such as polyhexamethylene adipamide textile materials, and, above all, aromatic polyester textile materials such as polyethylene terephthalate textile materials. Such materials can be in the form of filaments, fibres or woven or knitted materials.

The said azo dyestuffs can be applied to the synthetic textile materials by methods which are conventionally employed in applying disperse dyestuffs to such textile materials. Thus the dyestuffs in the form of aqueous dispersions can be applied by dyeing, padding or printing processes using the conditions and other additives which are conventionally used in carrying out such processes. Alternatively the said dyestuffs can be applied to synthetic textile materials by solvent methods of dyeing, for example by applying a solution or dispersion of the dyestuff in perchloroethylene optionally containing a minor amount of water to the textile material preferably at elevated temperature.

The dyestuffs may also be used to color synthetic polymers by melt coloration in particular by late injection techniques, and the colored polymers then melt spun into fibres or filaments. Alternatively the dyestuffs can be used to color synthetic textile materials by the process of transfer color printing.

When applied to synthetic textile materials the azo dyestuffs of the invention give orange to green colorations which have excellent fastness to light and to wet and to dry heat treatments, both before and after heat setting. The said dyestuffs also have high tinctorial strength and excellent dyeing and build-up properties on synthetic textile materials, particularly aromatic polyester textile materials, thus enabling heavy depths of shade to be readily obtained. When the said dyestuffs are applied to synthetic textile materials by exhaust dyeing methods they additionally exhaust well and have good levelling and temperature range properties. In addition the depths of shade obtained are relatively independent of the pH of the dyebath or the temperature of the dyebath or its liquor rate. When applied to aromatic polyester/cellulose unions any unfixed dyestuff on the said unions can be readily removed by a simple alkaline washing treatment.

The invention is illustrated but not limited by the following Examples in which the parts and percentages are by weight.

EXAMPLE 1.

7.6 Parts of sodium nitrite are added to 90 parts of sulphuric acid the temperature being allowed to rise to 30° C. The mixture is then cooled to 5° C. and a mixture of 50 parts of propionic acid and 300 parts of acetic acid is slowly added, the temperature being allowed to rise to 15° C. and then being maintained at this temperature. The solution is then cooled to 0° C., 18.9 parts of 2-amino-3:5-dinitrothiophene are added over 30 minutes and the mixture is stirred for 30 minutes at 0° C. The resulting solution is added to a solution of 27.9 parts of N:N-di(β-acetoxyethyl)aniline in 300 parts of water containing 30 parts of a concentrated aqueous solution of hydrochloric acid and 350 parts of ice. The mixture is stirred for 50 minutes at 0° C. and the precipitated dyestuff is filtered off, washed with water and dried.

When applied to aromatic polyester textile materials from an aqueous dispersion the dyestuff yields blue shades of excellent fastness properties.

When the above coupling component is replaced by an equivalent amount of N:N-di(β-acetoxyethyl)-m-toluidine a dyestuff is obtained which yields greenish-blue shades on aromatic polyester textile materials.

The 2-amino-3:5-dinitrothiophene used in the above Example was obtained by reacting the sodium salt of cyanoacetic acid with the dimer of mercaptoacetaldehyde in aqueous medium at 80° C., cooling to 20° C., adding acetic anhydride whilst maintaining the pH of the mixture between 6 and 7, acidifying and isolating the 2-acetylaminothiophene-3-carboxylic acid. This was then dinitrated in sulphuric acid medium at 0° C., the resulting 2-acetylamino-3:5-dinitrothiophene isolated and then deacylated by heating in an aqueous solution of sulphuric acid.

EXAMPLE 2

2.03 Parts of 2-amino-3:5-dinitro-4-methylthiophene are added to 3.8 parts of a 40% solution of nitrosylsulphuric acid in sulphuric acid which has been diluted with 9.6 parts of acetic acid 1.6 parts of propionic acid and 6 parts of sulphuric acid, and the mixture is stirred for 1 hour at 0° C. Excess nitrous acid is then destroyed by the addition of urea, and the resulting mixture is added to a solution of 2.79 parts of N:N-di(β-acetoxyethyl)-m-toluidine in a mixture of 50 parts of water, 25 parts of ice and 6 parts of a 2 N aqueous solution of hydrochloric acid. The pH of the mixture is then adjusted to 3 by the addition of sodium acetate, and the dyestuff which is precipitated is filtered off, washed with water and dried.

When applied to aromatic polyester textile materials from an aqueous dyebath, the dyestuff yields blue shades of excellent fastness properties.

The 2-amino-3:5-dinitro-4-methylthiophene was itself obtained as follows:

Chloroacetone was reacted with sodium hydrosulphide in aqueous methanol, and the resulting solution containing the reaction product treated with ethylcyanoacetate in the presence of triethylamine at the boil. Addition of water precipitated 2-amino-3-ethoxycarbonyl-4-methylthiophene which was reacted with acetic anhydride to give 2-acetylamino-3-ethoxycarbonyl-4-methylthiophene which on hydrolysis with an aqueous solution of sodium hydroxide was converted to 2- acetylamino-4-methylthiophene-3-carboxylic acid. This was decarboxylated by heating in N:N-diethylaniline at 220° C., and the resulting 2-acetylamino-4-methylthiophene dinitrated in sulphuric acid medium at −5° C. The resulting product was then heated in an aqueous solution of sulphuric acid to remove the N-acetyl group.

EXAMPLE 3

In place of the 18.9 parts of 2-amino-3:5-dinitrothiophene used in Example 1 there are used 23.4 parts of 2-amino-3:4:5-trinitrothiophene when similar dyestuffs are obtained.

The 2-amino-3:4:5-trinitrothiophene was obtained by reacting 2-bromo-3:4:5-trinitrothiophene (Journal of Organics Chemistry 1957 at page 1588) with ammonia in tetrahydrofuran.

EXAMPLE 4

In place of the 18.9 parts of 2-amino-3:5-dinitrothiophene used in Example 1 there are used 27.6 parts of 2-amino-3-nitro-5-(N:N-diethylcarbamoyl)thiophene when similar dyestuffs are obtained.

This thiophene compound was obtained by treating 2-bromo-3-nitrothiophene-5-carboxylic acid (Chemical Abstracts 1963 at page 3860h) with thionyl chloride in toluene in the presence of dimethylformamide, and subsequently reacting with diethylamine followed by treatment with ammonia to replace the bromine atom by an amino group.

EXAMPLE 5

In place of the 18.9 parts of 2-amino-3:5-dinitrothiophene used in Example 1 there are used 20.2 parts of 2-amino-3-nitro-5-methoxycarbonylthiophene when similar dyestuffs are obtained.

The above thiophene compound was obtained by esterifying 2-bromo-3-nitrothiophene-5-carboxylic acid by treatment with a 9% solution of sulphuric acid in methanol, and subjecting the bromoester to treatment with a concentrated aqueous solution of ammonia in the presence of dimethylformamide.

EXAMPLE 6

2-Amino-3-nitro-5-cyanothiophene is diazotized and coupled on to N-ethyl-N-(β-hydroxyethyl)-m-toluidine by the procedure described in Example 1 to give a dyestuff which dyes aromatic polyester textile materials in blue shades of excellent fastness properties.

The 2-amino-3-nitro-5-cyanothiophene was itself obtained as follows:

The oxime of 2-acetylamino-5-formylthiophene (Journal of the Chemical Society 1955 at page 1701) was converted to 2-acetylamino-5-cyanothiophene by treatment with acetic anhydride at the boil. The resulting compound was then nitrated at 40° C. in a mixture of acetic acid and acetic anhydride, and the nitro compound de-acetylated by heating it on solution of sodium hydroxide in aqueous methanol.

Table I gives further Examples of the dyestuffs of the invention having the formula:

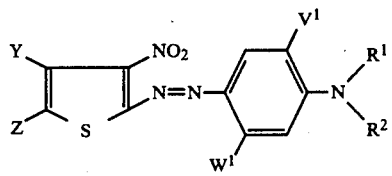

the symbols of which have the values given in the respective columns of the Table, the shade of the resulting dyeings when the dyestuffs are applied to an aromatic polyester textile material being given in the last column of Table. The dyestuffs of this Table were obtained by diazotizing the appropriate amines of the formula:

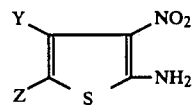

and coupling with the appropriate coupling component of the formula

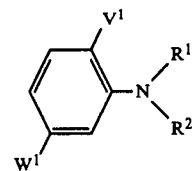

using methods similar to those described in Examples 1 and 2.

The amines of the above formula were obtained by analogous methods to those described under the previous Examples for the preparation of 2-amino-3-nitrothiophenes, but starting from the appropriate intermediates.

| EX. | Y | Z | V¹ | W¹ | R¹ | R² | SHADE |
|---|---|---|---|---|---|---|---|
| 7 | H | nitro | H | H | ethyl | β-hydroxyethyl | greenish-blue |
| 8 | " | " | " | H | methyl | methyl | greenish-blue |
| 9 | " | " | " | H | ethyl | ethyl | greenish-blue |
| 10 | " | " | " | H | H | " | blue |
| 11 | " | " | " | H | H | β-hydroxyethyl | " |
| 12 | " | " | " | H | H | β-acetoxyethyl | " |
| 13 | " | " | " | H | β-n-butyrloxyethyl | β-n-butryloxyethyl | " |
| 14 | " | " | " | H | β-iso-butyrloxyethyl | β-iso-butyrloxyethyl | " |
| 15 | " | " | " | H | ethyl | β-cyanoethyl | " |
| 16 | " | " | " | H | β-cyanoethyl | " | violet |
| 17 | " | " | " | H | β-cyanoethyl | β-(β'-methoxyethoxycarbonyl)ethyl | " |
| 18 | " | " | " | H | ethyl | β-methoxycarbonylethyl | greenish-blue |

-continued

| EX. | Y | Z | V¹ | W¹ | R¹ | R² | SHADE |
|---|---|---|---|---|---|---|---|
| 19 | " | " | " | H | ethyl | β-acetoxyethyl | greenish-blue |
| 20 | " | " | " | H | β-methoxycarbonylethyl | β-methoxycarbonylethyl | blue |
| 21 | " | " | " | H | β-ethoxycarbonylethyl | β-ethoxycarbonylethyl | " |
| 22 | " | " | " | H | ethyl | α-methyl-β-(methoxycarbonyl)ethyl | greenish-blue |
| 23 | " | " | " | H | ethyl | β-methyl-β-(butoxycarbonyl)ethyl | greenish-blue |
| 24 | " | " | " | H | ethyl | β-chloroethyl | greenish-blue |
| 25 | " | " | " | H | ethyl | γ-chloro-β-hydroxypropyl | greenish-blue |
| 26 | " | " | " | H | ethyl | β-(β'-cyanoethoxy)ethyl | greenish-blue |
| 27 | " | " | " | H | ethyl | β-(β'-methoxycarbonylethylthio)ethyl | greenish-blue |
| 28 | " | " | " | H | ethyl | β-(β'-ethoxycarbonylethoy)ethyl | greenish-blue |
| 29 | " | " | " | methyl | ethyl | 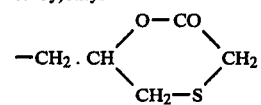 | greenish-blue |
| 30 | " | " | " | chlorine | β-acetoxyethyl | β-acetoxyethyl | reddish-blue |
| 31 | " | " | " | H | β-methoxyethyl | β-methoxyethyl | greenish-blue |
| 32 | " | " | " | methyl | β-hydroxyethyl | β-hydroxyethyl | bluish-green |
| 33 | " | " | methoxy | methoxy | β-acetoxyethyl | β-acetoxyethyl | green |
| 34 | " | " | H | methoxy | ethyl | ethyl | " |
| 35 | " | " | " | bromine | ethyl | " | blue |
| 36 | " | " | " | H | ethyl | β-(chloroacetoxy)ethyl | greenish-blue |
| 37 | " | " | " | methyl | ethyl | β-(β'-methoxypropionyloxy)ethyl | greenish-blue |
| 38 | " | " | methoxy | methoxy | H | H | greenish-blue |
| 39 | " | " | methyl | methoxy | H | H | greenish-blue |
| 40 | " | " | methoxy | methyl | ethyl | ethyl | green |
| 41 | " | " | H | methyl | ethyl | ω-hydroxybutyl | bluish-green |
| 42 | " | " | " | H | ethyl | ω-acetoxybutyl | greenish-blue |
| 43 | " | " | methyl | methyl | H | β-hydroxyethyl | greenish-blue |
| 44 | " | " | H | H | n-dodecyl | " | greenish-blue |
| 45 | " | " | " | H | β-(p-bromobenzoyloxy)ethyl | β-(p-bromobenzoyloxy)ethyl | blue |
| 46 | " | " | methyl | H | β-hydroxyethyl | β-hydroxyethyl | greenish-blue |
| 47 | " | " | chlorine | H | β-hydroxyethyl | " | blue |
| 48 | " | " | H | H | ethyl | β-(cyanomethoxycarbonyl)ethyl | " |
| 49 | " | " | " | H | H | β-methoxycarbonylethyl | " |
| 50 | " | " | " | H | β-hydroxyethyl | β-phenylethyl | " |
| 51 | " | " | chlorine | H | β-acetoxyethyl | β-acetoxyethyl | " |
| 52 | " | " | H | H | β-(β'-methoxyethoxycarbonyl)ethyl | β-(β-methoxyethoxycarbonyl)ethyl | " |
| 53 | " | " | " | methyl | β-formyloxyethyl | β-formyloxyethyl | " |
| 54 | " | " | " | methyl | β-(ethoxycarbonylmethylaminocarbonyloxy)ethyl | β-(ethoxycarbonylmethylaminocarbonyloxy)ethyl | " |
| 55 | " | " | " | methyl | ethyl | β-acetylethyl | greenish-blue |
| 56 | " | " | " | H | ethyl | ω-hydroxypentyl | greenish-blue |
| 57 | " | " | " | H | ethyl | β-chloro-γ-(p-chlorophenoxy)propyl | greenish-blue |
| 58 | " | " | " | methyl | β-(methylsulphonyloxy)ethyl | β-(methylsulphonyloxy)ethyl | blue |
| 59 | " | " | " | methyl | β-cyanoethyl | β-phenoxyethyl | " |
| 60 | " | " | " | ethoxycarbonylmethyl | ethyl | ethyl | greenish-blue |
| 61 | " | " | " | methoxymethyl | ethyl | ethyl | greenish-blue |
| 62 | " | " | ethoxycarbonylmethoxy | ethoxycarbonylmethoxy | H | H | greenish-blue |

-continued

| EX. | Y | Z | V¹ | W¹ | R¹ | R² | SHADE |
|---|---|---|---|---|---|---|---|
| 63 | " | " | methyl | ethylthio | ethyl | ethyl | greenish-blue |
| 64 | " | " | H | ethoxycarbonyl | ethyl | ethyl | blue |
| 65 | " | " | " | H | ethyl | β-(ethoxycarbonyloxy)ethyl | greenish-blue |
| 66 | " | " | " | benzoyloxy | ethyl | ethyl | bluish green |
| 67 | " | " | " | methylsulphonyloxy | ethyl | ethyl | greenish-blue |
| 68 | " | " | " | H | ethyl | α:β-di(ethoxycarbonyl)ethyl | greenish-blue |
| 69 | " | " | " | methoxycarbonyl-methylthio | ethyl | ethyl | greenish-blue |
| 70 | " | " | " | H | ethyl | p-methoxycarbonylbenzyl | greenish-blue |
| 71 | " | " | " | H | ethyl | phenyl | greenish-blue |
| 72 | " | " | " | H | H | cyclopentyl | blue |
| 73 | " | " | " | acetyl | β-acetoxyethyl | β-acetoxyethyl | " |
| 74 | " | " | " | methylsulphonyl | H | ethyl | violet |
| 75 | " | " | " | cyano | ethyl | ethyl | blue |
| 76 | " | " | " | methyl | ethyl | β-(β'-methoxyethoxycarbonyloxy)ethyl | greenish-blue |
| 77 | " | " | " | trifluoromethyl | H | β-cyanoethoxyethyl | blue |
| 78 | " | " | " | H | H | β:β-dimethylethyl | " |
| 79 | " | " | " | N-ethylsulphonyl | ethyl | ethyl | violet |
| 80 | " | " | " | methylsulphonyl-amino | ethyl | ethyl | greenish-blue |
| 81 | " | " | " | methylsulphonyl-amino | ethyl | β-(methylaminosulphonyl)ethyl | greenish-blue |
| 82 | " | " | " | methylsulphonyl-amino | ethyl | ethyl | blue |
| 83 | " | " | " | N-ethylcarbamoyl | ethyl | methyl | " |
| 84 | " | " | " | H | methyl | N-methylsulphonyl-β-p-anisidinoethyl | greenish-blue |
| 85 | " | " | " | methyl | ethyl | β-[β'-methoxyethoxy)ethoxycarbonyl]ethyl | greenish-blue |
| 86 | " | " | " | H | ethyl | m-methylsulphonylbenzyl | greenish-blue |
| 87 | " | " | " | methyl | β-phenoxyethyl | —C₂H₄OCONHCH₂COOCH₃ | greenish-blue |
| 88 | methyl | " | " | methyl | β-acetoxyethyl | β-acetoxyethyl | blue |
| 89 | " | " | " | H | H | β-cyanoethyl | violet |
| 90 | " | " | " | H | H | cyclopentyl | blue |
| 91 | " | " | " | H | β-cyanoethyl | β-(m-methoxyphenoxycarbonyl)ethyl | violet |
| 92 | " | " | methyl | methoxy | H | H | blue |
| 93 | " | " | H | chlorine | β-methoycarbonylethyl | β-methoxycarbonylethyl | violet |
| 94 | " | " | " | H | H | β-β'-acetoxyethoxy)ethyl | blue |
| 95 | p-nitrophenyl | " | " | methyl | β-acetoxyethyl | β-acetoxyethyl | bluish-green |
| 96 | H | methoxycarbonyl | " | methyl | β-acetoxyethyl | " | violet |
| 97 | " | methoxycarbonyl | " | methyl | ethyl | β-cyanoethyl | red |
| 98 | " | β-methoxyethoxycarbonyl | " | methyl | ethyl | ethyl | violet |
| 99 | " | cyano | " | H | methyl | β-methoxycarbonylethyl | bluish red |
| 100 | " | " | " | methyl | ethyl | β-acetoxyethyl | violet |
| 101 | " | " | " | methyl | β-(β'-methoxyethoxycarbonyl)ethyl | β-(β'-methoxyethoxycarbonyl)ethyl | " |
| 102 | " | " | " | methyl | β-acetoxyethyl | β-acetoxyethyl | " |
| 103 | " | carbamoyl | " | methyl | β-acetoxyethyl | " | " |
| 104 | " | N-phenylcarbamoyl | " | methyl | β-acetoxyethyl | " | " |
| 105 | " | N-ethylcarbamoyl | " | methyl | β-acetoxyethyl | " | " |
| 106 | p-nitrophenyl | isopropyl | " | H | β-acetoxyethyl | β-acetoxyethyl | blue |
| 107 | p-nitrophenyl | 2-nitro-4-methylphenyl | " | H | β-hydroxyethyl | ethyl | " |
| 108 | H | nitro | " | H | propyl | benzyl | " |
| 109 | " | " | " | H | α-methyl-β-ethoxy carbonylethyl | H | " |
| 110 | " | " | " | H | β-methoxycarbonylethyl | benzyl | " |
| 111 | " | " | " | H | β-(β'-methoxyethoxy carbonyl) | benzyl | " |
| 112 | " | " | " | chlorine | β-propionyloxyethyl | ethyl | " |

-continued

| EX. | Y | Z | V¹ | W¹ | R¹ | R² | SHADE |
|---|---|---|---|---|---|---|---|
| 113 | " | " | chlorine | H | H | β-(β-carbamoylethoxy)ethyl | " |
| 114 | " | " | methoxy | H | H | β-(β'-ethoxycarbonylethoxy) ethyl | bluish-green |
| 115 | " | " | methyl | methyl | H | β-methoxycarbonylethyl | blue |
| 116 | " | " | chlorine | methyl | H | β-(β'-ethoxycarbonylethoxy) ethyl | blue |
| 117 | " | " | H | methoxycarbonyl | β-methoxycarbonylethyl | β-methoxycarbonylethyl | blue |
| 118 | " | " | " | methoxycarbonyl | ethyl | β-acetoxyethyl | " |
| 119 | " | " | " | methylsulphonyl | β-acetoxyethyl | " | violet |
| 120 | " | " | " | methylsulphonyl | ethyl | ethyl | blue |
| 121 | " | " | " | acetyl | β-methoxycarbonyl | β-methoxycarbonyl | " |
| 122 | " | " | " | cyano | β-acetoxyethyl | β-acetoxyethyl | violet |
| 123 | " | " | " | methylthio | ethyl | ethyl | blue |
| 124 | " | " | " | methylthio | β-acetoxyethyl | β-acetoxyethyl | " |
| 125 | " | " | " | N-methylcarbonamido | β-acetoxyethyl | " | " |
| 126 | " | " | " | N-methylcarbonamido | ethyl | " | " |
| 127 | " | " | " | N-methylcarbonamido | ethyl | ethyl | " |

We claim:

1. A disperse monoazo dystuff, free from carboxylic and sulphonic acid groups, which is of the formula:

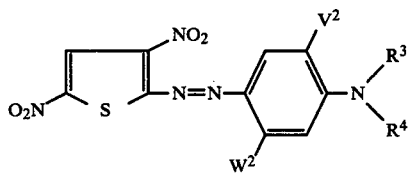

wherein V² is selected from the group consisting of hydrogen, lower alkyl and lower alkoxy;

W² is selected from the group consisting of hydrogen, lower alkyl, lower alkoxy, chlorine, bromine and trifluoromethyl;

R³ is selected from the group consisting of hydrogen, lower alkyl, cyano lower alkyl, lower alkyl carbonyloxy lower alkyl, lower alkoxycarbonyl lower alkyl, lower alkoxy lower alkoxycarbonyl lower alkyl, lower alkoxy lower alkyl and phenyl lower alkyl;

and R⁴ is selected from the group consisting of lower alkyl, hydroxy lower alkyl, cyano lower alkyl, lower alkyl carbonyloxy lower alkyl, lower alkoxy carbonyl lower alkyl, lower alkoxy lower alkoxy carbonyl lower alkyl, lower alkoxy lower alkoxy lower alkoxycarbonyl lower alkyl, lower alkoxy lower alkyl and phenyl lower alkyl.

2. A disperse monozao dyestuff, free from carboxylic and sulphonic acid groups which is of the formula:

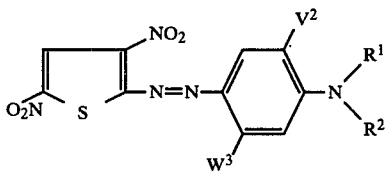

wherein V² is selected from the group consisting of hydrogen, lower alkyl and lower alkoxy; W³ is selected from the group consisting of hydrogen, lower alkyl, lower alkoxy, chlorine and bromine; R¹ is selected from the group consisting of hydrogen, lower alkyl, cyano lower alkyl, lower alkoxy lower alkyl, lower alkoxy lower alkoxy lower alkyl, hydroxy lower alkyl, lower alkylcarbonyloxy lower alkyl, lower alkoxycarbonyl lower alkyl, lower alkoxy lower alkoxy carbonyl lower alkyl, benzoyloxy lower alkyl, lower alkoxy lower alkoxy lower alkoxy carbonyl lower alkyl, lower alkoxy carbonyl lower alkylamino carbonyloxy lower alkyl, lower alkylsulphonyloxy lower alkyl, phenyl lower alkyl and phenoxy lower alkyl; and R² is selected from the group consisting of hydrogen, lower alkyl, hydroxy lower alkyl, cyano lower alkyl, lower alkylcarbonyl lower alkyl, lower alkylcarbonyloxy lower alkyl, hydroxy lower alkoxy lower alkyl, lower alkoxycarbonyl lower alkyl, lower alkoxy lower alkoxycarbonyl lower alkyl, lower alkoxy lower alkoxy lower alkoxycarbonyl lower alkyl, chloro lower alkyl, chloro hydroxypropyl, cyano lower alkoxy lower alkyl, lower alkoxycarbonyl lower alkoxy lower alkyl, lower alkoxy lower alkyl, lower alkoxy lower alkoxy lower alkyl, chloro lower alkylcarbonyloxy lower alkyl, hydroxy lower alkoxy lower alkyl, lower alkoxy lower alkyl carbonyloxy lower alkyl, phenyl lower alkyl, phenoxy lower alkyl, lower alkylsulphonyloxy lower alkyl, lower alkoxycarbonyloxy lower alkyl, lower alkoxycarbonyl lower alkylaminocarbonyloxy lower alkyl, lower alkylamino sulphonyl lower alkyl, di(lower alkoxycarbonyl) lower alkyl, phenyl, cyclopentyl, phenoxycarbonyl lower alkyl, lower alkylcarbonyl lower alkoxy lower alkyl, benzoyloxy lower alkyl and cyano lower alkoxy carbonyl lower alkyl.

3. A disperse monoazo dyestuff, free from carboxylic and sulphonic acid groups, which is of the formula:

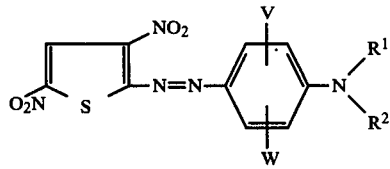

wherein V is selected from the group consisting of hydrogen, chlorine, lower alkyl, lower alkoxy and lower alkoxy carbonyl lower alkoxy; W is selected from the group consisting of hydrogen, chlorine, bromine, lower alkyl, lower alkoxy lower alkyl, lower alkoxy carbonyl lower alkyl, lower alkoxy, lower alkoxycarbonyl lower alkoxy, lower alkylthio, lower alkoxycarbonyl lower alkylthio, lower alkoxy carbonyl, cyano, trifluoromethyl, lower alkylcarbonyl, lower alkylsulphonyl, benzoyloxy, lower alkylcarbonyloxy, and N- lower alkyl carbonamido; R¹ is selected from the group consisting of hydrogen, lower alkyl, cyano lower alkyl, lower alkoxy lower alkyl, lower alkoxy lower alkoxy lower alkyl, hydroxy lower alkyl, lower alkylcarbonyloxy lower alkyl, lower alkoxycarbonyl lower alkyl, lower alkoxy lower alkoxy carbonyl lower alkyl, benzoyloxy lower alkyl, lower alkoxy lower alkoxy lower alkoxy carbonyl lower alkyl, lower alkoxy carbonyl lower alkylaminocarbonyloxy lower alkyl, lower alkylsulphonyloxy lower alkyl, phenyl lower alkyl and phenoxy lower alkyl; and R² is selected from the group consisting of hydrogen, lower alkyl, hydroxy lower alkyl, cyano lower alkyl, lower alkylcarbonyl lower alkyl, lower alkylcarbonyloxy lower alkyl, hydroxy lower alkoxy lower alkyl, lower alkoxycarbonyl lower alkyl, lower alkoxy lower alkoxycarbonyl lower alkyl, lower alkoxy lower alkoxy lower alkoxybarbonyl lower alkyl, chloro lower alkyl, chloro hydroxypropyl, cyano lower alkoxy lower alkyl, lower alkoxycarbonyl lower alkoxy lower alkyl, lower alkoxy lower alkyl, lower alkoxy lower alkoxy lower alkyl, chloro lower alkylcarbonyloxy lower alkyl, hydroxy lower alkoxy lower alkyl, lower alkoxy lower alkyl carbonyloxy lower alkyl, phenyl lower alkyl, phenoxy lower alkyl, lower alkylsulphonyloxy lower alkyl, lower alkoxycarbonyloxy lower alkyl, lower alkoxycarbonyl lower alkylaminocarbonyloxy lower alkyl, lower alkylamino sulphonyl lower alkyl, di(lower alkoxycarbonyl)-lower alkyl, phenyl, cyclopentyl, phenoxycarbonyl lower alkyl, lower alkylcarbonyloxy lower alkoxy lower alkyl, benzoyloxy lower alkyl and cyano lower alkoxy carbonyl lower alkyl.

* * * * *